(12) United States Patent
Gordon et al.

(10) Patent No.: US 11,353,449 B2
(45) Date of Patent: Jun. 7, 2022

(54) (1→3)-β-D-GLUCAN AS A MEASURE OF ACTIVE MOLD

(71) Applicant: Inspirotec, Inc., Lake Bluff, IL (US)

(72) Inventors: Julian Gordon, Lake Bluff, IL (US); Rachel Reboulet, Chicago, IL (US)

(73) Assignee: Inspirotec, Inc., Glenview, IL (US)

( * ) Notice: Subject to any disclaimer, the term of this patent is extended or adjusted under 35 U.S.C. 154(b) by 387 days.

(21) Appl. No.: 16/012,289

(22) Filed: Jun. 19, 2018

(65) Prior Publication Data

US 2018/0364218 A1 Dec. 20, 2018

Related U.S. Application Data

(60) Provisional application No. 62/521,677, filed on Jun. 19, 2017.

(51) Int. Cl.
*G01N 33/53* (2006.01)
*G01N 1/22* (2006.01)
*G01N 1/40* (2006.01)

(52) U.S. Cl.
CPC ....... *G01N 33/5308* (2013.01); *G01N 1/2202* (2013.01); *G01N 1/2205* (2013.01); *G01N 1/2208* (2013.01); *G01N 1/2247* (2013.01); *G01N 1/4055* (2013.01); *G01N 2001/225* (2013.01); *G01N 2400/24* (2013.01)

(58) Field of Classification Search
CPC .. G01N 1/2202; G01N 1/2205; G01N 1/2208; G01N 1/2247; G01N 1/4055; G01N 2001/225; G01N 2400/24; G01N 33/5308; B03C 2201/14; B03C 2201/26; B03C 3/08; B03C 3/12; B03C 3/017; B03C 3/41; B03C 3/47; B03C 2201/04

USPC .... 435/7.21, 6.15, 7.2, 287.2; 436/177, 178, 436/181, 815; 422/83, 88

See application file for complete search history.

(56) References Cited

U.S. PATENT DOCUMENTS

| | | | |
|---|---|---|---|
| 5,266,461 A | 11/1993 | Tanaka | |
| 9,360,402 B2* | 6/2016 | Gordon | G01N 1/40 |
| 2011/0185904 A1* | 8/2011 | Langle | B01D 46/42 96/19 |

(Continued)

FOREIGN PATENT DOCUMENTS

| WO | WO 1983/002123 | 6/1983 |
|---|---|---|
| WO | WO 2012/0894171 | 7/2012 |

OTHER PUBLICATIONS

Sander (2008) J Imm Meth 337:55-62 (Year: 2008).*

*Primary Examiner* — Christopher L Chin
(74) *Attorney, Agent, or Firm* — Wood, Phillips, Katz, Clark & Mortimer

(57) ABSTRACT

Electrokinetic devices and methods are described with the purpose of collecting assayable agents from a dielectric fluid medium. Electrokinetic flow may be induced by the use of plasma generation at high voltage electrodes and consequent transport of charged particles in an electric voltage gradient. Actively growing mold releases the carbohydrate cell wall component (1→3)-β-D-Glucan into the air. The invention recognizes that the airborne fraction is that which affects respiratory health and selectively tests for a free form which is soluble in aqueous medium. The sample to be analysed is preferably collected by the electrokinetic propulsion method described, but any air sampling method such as filtration, impactor or impingement may be applicable.

11 Claims, 5 Drawing Sheets

(56) References Cited

U.S. PATENT DOCUMENTS

Figure 1:
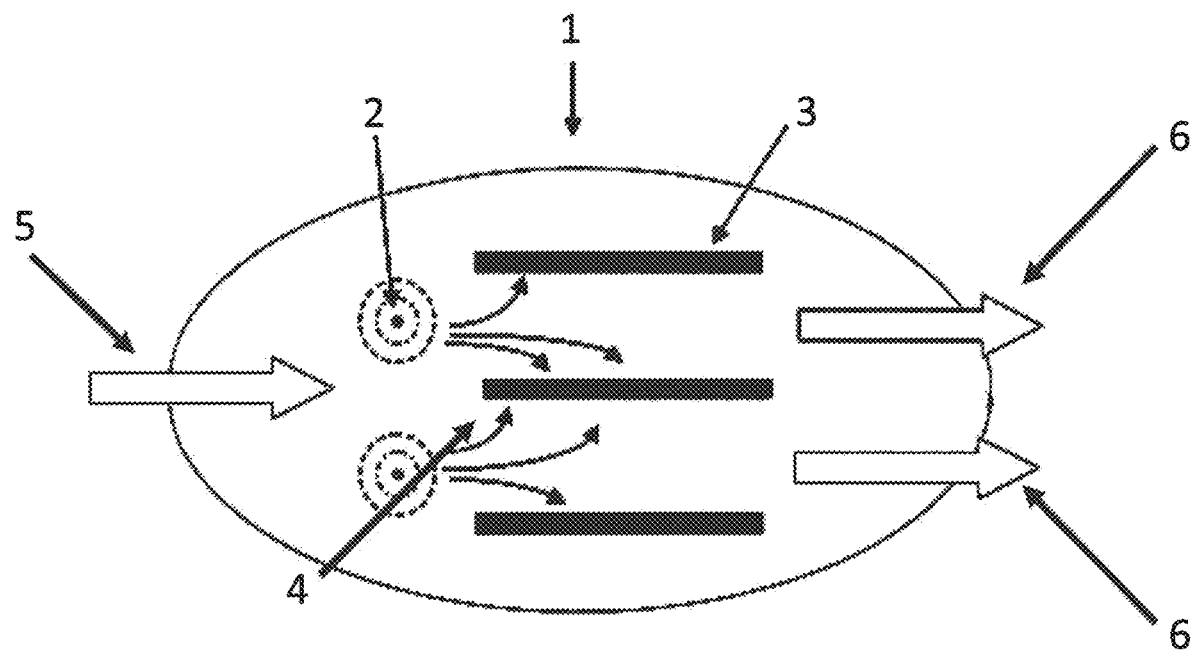
Figure 2:
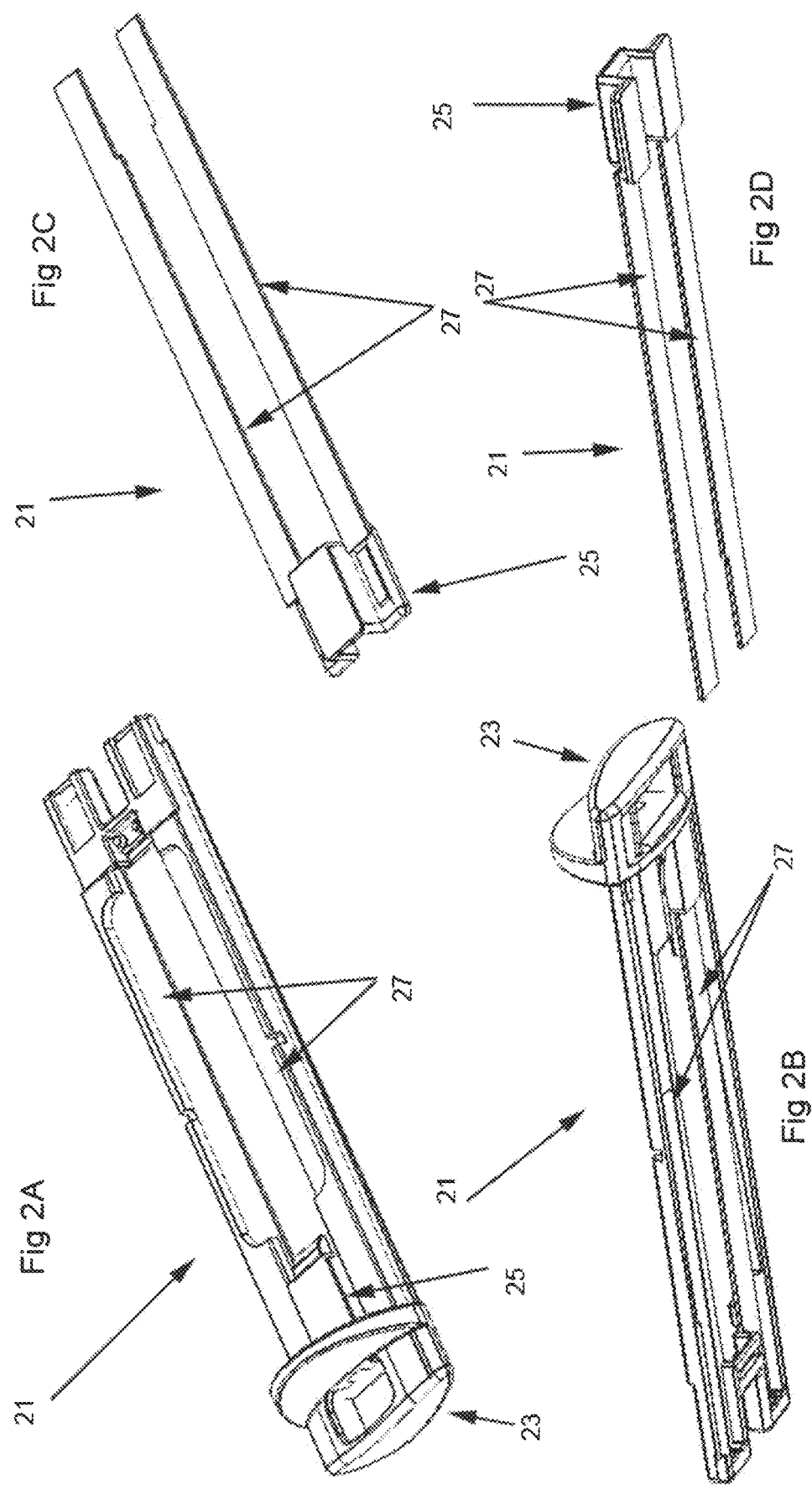

| | | | | |
|---|---|---|---|---|
| 2012/0174650 A1* | 7/2012 | Ariessohn | ............... | B08B 7/026 |
| | | | | 73/23.2 |
| 2013/0119152 A1* | 5/2013 | Wishneski | ............ | B29B 7/7404 |
| | | | | 239/128 |
| 2015/0118676 A1* | 4/2015 | Gordon | ................ | G01N 1/2202 |
| | | | | 435/5 |

* cited by examiner

(1→3)-β-D-GLUCAN AS A MEASURE OF ACTIVE MOLD

BACKGROUND OF THE INVENTION

Field of the Invention

The present invention relates to the collection of and sampling of assayable agents in a dielectric medium. This includes, but is not limited to, sampling air for agents whose presence or absence is determinable by bio-specific assays for mold or mold spore cell wall components. The field includes sampling of air for biological agents, direction to, and deposition on, a collection means for an assay device. The agent-specific assays may include immunoassays or chromogenic assays based on proteolytic pathways. Assays may include, but are not limited to, detection means which are colorometric, fluorescent, turbidimetric, electrochemical or voltammetric.

Description of the Prior Art (1→3)-β-d-glucan, like allergens (1-3) are present in spores but are released into air by germinating and growing fungi in particulate form not readily recognizable microscopically as spores. Thus, while (1→3)-β-d-glucan itself is not an allergen, the two are likely to be associated in the air. (1→3)-β-d-glucan is also found in pollen (4).

Structure:

(1→3)-β-D-glucan are non-allergenic water-insoluble structural cell wall components of most fungi, some bacteria, most higher plants and many lower plants. Glucans may account for up to 60% of the dry weight of the cell wall of fungi, of which the major part is (1→3)-β-D-glucan (Klis, 1994). They consist of glucose polymers with variable molecular weight and degree of branching i.e. triple helix, single helix or random coil structures (Williams, 1997). In the fungal cell wall, (1→3)-β-D-glucans are linked to proteins, lipids and carbohydrates such as mannan and chitin, and they contain (1→3)-b-glucan side-branches which may connect with adjacent (1→3)-β-D-glucan polymers.

Relation to Symptoms:

Levels in air correlate with fungal mass and severity of symptoms. This is not a causal relationship because of contribution of allergens released from fungi (5). B-glucan correlates with Peak Respiratory Flow Variability (PFV) in children with 50% having pre-existing respiratory conditions (6).

Douwes reviewed literature pertaining to B-glucan and respiratory health (7). They concluded the studies reviewed suggested some association between (1→3)-β-D-glucan exposure, airway inflammation and symptoms. Potential underlying inflammatory mechanisms associated with exposure could not be identified. Population studies and animal and human studies using experimental exposure are included.

Assays:

Three kinds of assay have been used in the literature: inhibition immunoassay immunoassay (8), sandwich monoclonal immunoassay (9) and limulus amebocyte assay. The latter is commercialized by Associates of Cape Cod. Brooks et al (10) did an inter-laboratory comparison of the 3 methods. Results obtained with different methods were often significantly correlated and therefore comparable in relative terms, but direct comparison of results between laboratories and assays is inappropriate.

Extraction:

Most β-(1,3)-glucans are water insoluble at ambient temperature, and two extraction methods either alkali extraction (typically vortex followed by 1 hr shaking in 0.3N NaOH) and hot water extraction (typically 0.05% TWEEN® 20 (TWEEN is a registered trademark of CRODA AMERICAS LLC) in PBS, end-over-end rotation, autoclave 60 min vortex). Alkaline extraction has been used in limulus amebocyte-based methods, and heat extraction with EIA-based methods. Extraction methods used are reviewed in (10). Measurements on spores from filters (11) were done including treatment with 0.15N NaOH. Followed by neutralization with equal volume tris-CI at twice the normality of the NaOH. Not all papers mention the neutralizations step. No extraction was mentioned in the pollen publication (4).

Madsen et al described optimization of extraction with NaOH (12) and reviewed some work where extraction is or is not used or not mentioned. No controls were done in this or other work with no extraction. It is frequently stated that the extraction is required to solubilize the (1→3)-β-D-glucan.

Size Range:

Foto et al did a study with extensive samples from damaged homes (13). They state that (1→3)-β-D-glucan is associated with fragments, hyphae as well as spores. No actual direct data was given. Lee et al (14). did an indoor to outdoor comparison of (1→3)-β-D-glucan. They also mention fragments but provide no data. Saleres et al (15). found in airborne fraction a smaller size range than intact spores, which, they say, implies deeper lung penetration. Madsen et al (16) found a large fraction of (1-3)-β-D-glucan in the PM1 fraction which contained no spores. In spite of the small size, they still say material was "made water soluble" using 0.3M NaOH.

Singh et al (17, 18) did size fractionation with the NIOSH sampler, and found equal amounts (1→3)-β-D-glucan in 3 size cuts going down to PM1 fraction.

Chen et al compared inside v. outside and effect of human activity (19, 20). They found the smallest size was least affected by human activity but more (1-3)-β-D-glucan in larger size particles.

Surrogate Assay:

Vogelmark et al (21) did measurements on *Penicillium, Aspergillus*, Stachrybotis cultures for spores. They do not mention any extraction method. They recommend (1→3)-β-D-glucan measurement as surrogate for mold exposure.

Chew et al (22) used vacuumed dust extract (22)(21) and did correlation of (1→3)-β-D-glucan with viable spores. They say dust is a surrogate for airborne exposure.

Speciation:

Iossifova et al compared with mold species in dust using EPA standard multiplex qPCR for molds (23). There was no correlation between (1→3)-β-D-glucan with Relative Moldiness Index (RMI) derived from the from the qPCR. They used complicated multivariate statistical analysis to show correlation with the predominant species. *Cladosporium* and *Aspergillus* genera, as well as *Epicoccum nigrum, Penicillium brevicompactum* and *Wallemia sebi*. contributors There was no correlation with *Alternaria*. This does not mean *Alternaria* produces no (1→3)-β-D-glucan.

LIST OF REFERENCES

1. Green B J, Schmechel D, Summerbell R C. Aerosolized fungal fragments. Adan O C G, Samson R A, editors. Wageningen: Wageningen Acad Publ; 2011.

2. Green B J, Tovey E R, Sercombe J K, Blachere F M, Beezhold D H, Schmechel D. Airborne fungal fragments and allergenicity. Medical Mycology. 2006 September; 44:S245-S55.
3. Green B J, Mitakakis T Z, Tovey E R. Allergen detection from 11 fungal species before and after germination. J Allergy Clin Immunol. [Article]. 2003 February; 111(2): 285-9.
4. Rylander R, Fogelmark B, McWilliam A, Currie A. (1->3)-beta-D-glucan may contribute to pollen sensitivity. Clin Exp Immunol. 1999 March; 115(3):383-4.
5. Rylander R. Indoor air-related effects and airborne (1->3)-beta-D-glucan. Environ Health Perspect. 1999 June; 107: 501-3.
6. Douwes J, Zuidhof A, Doekes G, van der Zee S, Wouters I, Boezen H M, et al. (1->3)-beta-D-glucan and endotoxin in house dust and peak flow variability in children. American Journal of Respiratory and Critical Care Medicine. [Article]. 2000 October; 162(4):1348-54.
7. Douwes J. (1->3)-beta-D-glucans and respiratory health: a review of the scientific evidence. Indoor Air. 2005 June; 15(3):160-9.
8. Douwes J, Doekes G, Montijn R, Heederik D, Brunekreef B. Measurement of beta (1->3)-glucans in occupational and home environments with an inhibition enzyme immunoassay. Applied and Environmental Microbiology. 1996 September; 62(9):3176-82.
9. Sander I, Fleischer C, Borowitzki G, Bruning T, Raulf-Heimsoth M. Development of a two-site enzyme immunoassay based on monoclonal antibodies to measure airborne exposure to (1->3)-beta-D-glucan. Journal of Immunological Methods. 2008 August; 337(1):55-62.
10. Brooks C R, Siebers R, Crane J, Noss I, Wouters I M, Sander I, et al. Measurement of beta-(1,3)-glucan in household dust samples using Limulus amebocyte assay and enzyme immunoassays: an inter-laboratory comparison. Environmental Science-Processes & Impacts. 2013; 15(2):405-11.
11. Foto M, Plett J, Berghout J, Miller J D. Modification of the Limulus amebocyte lysate assay for the analysis of glucan in indoor environments. Anal Bioanal Chem. 2004 May; 379(1):156=62.
12. Madsen A M, Frederiksen M W, Allermann L, Peitersen J H. (1->3)-beta-D-glucan in different background environments and seasons. Aerobiologia. [Article]. 2011 June; 27(2):173-9.
13. Foto M, Vrijmoed L L P, Miller J D, Ruest K, Lawton M, Dales R E. A comparison of airborne ergosterol, glucan and Air-O-Cell data in relation to physical assessments of mold damage and some other parameters. Indoor Air. 2005 August; 15(4):257-66.
14. Lee T, Grinshpun S A, Kim K Y, Iossifova Y, Adhikari A, Reponen T. Relationship between indoor and outdoor airborne fungal spores, pollen, and (1->3)-beta-D-glucan in homes without visible mold growth. Aerobiologia. 2006 September; 22(3):227-36.
15. Salares V R, Hinde C A, Miller J D. Analysis of Settled Dust in Homes and Fungal Glucan in Air Particulate Collected during HEPA Vacuuming. Indoor and Built Environment. [Article]. 2009 December; 18(6):485-91.
16. Madsen A M, Schlunssen V, Olsen T, Sigsgaard T, Avci H. Airborne Fungal and Bacterial Components in PM1 Dust from Biofuel Plants. Ann Occup Hyg. 2009 October; 53(7):749-57.
17. Singh U, Reponen T, Cho K J, Grinshpun S A, Adhikari A, Levin L, et al. Airborne Endotoxin and beta-D-glucan in PM1 in Agricultural and Home Environments. Aerosol and Air Quality Research. 2011 August; 11(4):376-86.
18. Singh U, Levin L, Grinshpun S A, Schaffer C, Adhikari A, Reponen T. Influence of home characteristics on airborne and dustborne endotoxin and beta-D-glucan. J Environ Monit. [Article]. 2011 November; 13(11):3246-53.
19. Chen Q, Hildemann L M. The Effects of Human Activities on Exposure to Particulate Matter and Bioaerosols in Residential Homes. Environ Sci Technol. 2009 July; 43(13):4641-6.
20. Chen Q, Hildemann L M. Size-Resolved Concentrations of Particulate Matter and Bioaerosols Inside versus Outside of Homes. Aerosol Sci Technol. 2009; 43(7):699-713.
21. Fogelmark B, Rylander R. (1->3)-beta-D-glucan in some indoor air fungi. Indoor and Built Environment. 1997 September-October; 6(5):291-4.
22. Chew G L, Douwes J, Doekes G, Higgins K M, van Strien R, Spithoven J, et al. Fungal extracellular polysaccharides, beta (1->3)-glucans and culturable fungi in repeated sampling of house dust. Indoor Air-International Journal of Indoor Air Quality and Climate. 2001 September; 11(3):171-8.
23. Iossifova Y, Reponen T, Sucharew H, Succop P, Vesper S. Use of (1-3)-beta-D-glucan concentrations in dust as a surrogate method for estimating specific fungal exposures. Indoor Air. 2008 June; 18(3):225-32.

U.S. Pat. No. 5,266,461, Tanaka, Method for determining (1→3)-β-D-glucan, is the only patent for assay of (1→3)-β-D-glucan that we are aware of. They use an antibody to inhibit the pathway for endotoxin sensitive factor.

In the prior art, there exist many examples of collection of agents from the air for bioassay. For example, the following publications describe various methods of allergen, pathogen and toxin collection for assay:

1. Yao et at (2009) in Aerosol Science volume 40, pages 492-502.
2. Noss et al (2008) in Applied and Environmental Microbiology, volume 74, pages 5621-5627.
3. King et al (2007) in Journal of Allergy and Clinical Immunology, volume 120, pages 1126-31.
4. Earle et al (2007) in Journal of Allergy and Clinical Immunology, volume 119, pages 428-433.
5. Peters et al (2007) in Journal of Urban Health: Bulletin of the New York Academy of Medicine, volume 84, pages 185-197.
6. Yao and Mainelis (2006) in Journal of Aerosol Science, volume 37, pages 513-527.
7. Platts-Mills et al (2005) in Journal of Allergy and Clinical Immunology, volume 116, pages 384-389.
8. Sercombe et al (2004) in Allergy, volume 60, pages 515-520.
9. Custis et al (2003) in Clinical and Experimental Allergy, volume 33, pages 986-991.
10. Polzius et al (2002) in Allergy, volume 57, pages 143-145.
11. Tsay et al (2002) in Clinical and Experimental Allergy, volume 32, pages 1596-1601.
12. Parvaneh et al (2000) in Allergy, volume 55, pages 1148-1154.
13. McNerney et al (2010) in BMC Infectious Diseases, volume 10, pages 161-166 and device in U.S. Pat. No. 7,384,793.

Other known methods of sample collection include trapping of volatile organic compounds (VOC) on activated carbon, de-sorption and analysis by mass spectrometry. See Phillips et al (2010) in Tuberculosis, volume 90, pages 145-151 and references therein. VOC's are not considered encompassed by the present invention since the assays are strictly chemical in nature, and are not bio-specific as defined here. By bio-specific is meant assays wherein the result is determined by a biological specificity such as nucleic acid specificity, antibody specificity, receptor-ligand specificity and the like. While diagnostic specificity may be achieved by VOC analysis, this is inferred by presence and amount of groups of defined organic compounds.

The foregoing prior art publications describe "dry" methods using pumping and filtration, wiping, passive deposition, electrokinetic transport etc; usually followed by an extraction step and application of the extract to an assay.

Methods for collection in a liquid stream have been described in the patent literature:
Yuan and Lin in US Patent Application 2008/0047429A1.
Saski et al in U.S. Pat. No. 6,484,594 issued in 2002.

While efficiently collecting agents from the air, such liquid streaming systems inevitably result in high dilution of the sample. There is a consequent trade-off in sensitivity unless the agents are re-concentrated.

Northrup et al in U.S. Pat. Nos. 7,705,739 and 7,633,606 describe an autonomously running system for air sampling and determination of airborne substances therein. They do not specify the exact method of air sampling, nor detail how it is transferred to an assay system.

There exist numerous commercially available systems for air purification based on filtration or electrostatic precipitation. For a general description see the Environmental Protection Agency article "Guide to Air Cleaners in the Home", U.S. EPA/OAR/ORIA/indoor Environments Division (MC-6609J) EPA 402-F-08-004, May 2008. Numerous commercial examples of systems exist using either High Efficiency Particulate Air (HEPA) filters or electrostatic precipitation filters. Such systems are widely used for removal of particulate matter or allergens from air, including as part of domestic heating, ventilation and air conditioning (HVAC) systems. HEPA filters have the advantage of removal of particles down to the micron size range, whereas electrostatic precipitation methods have the advantage of entailing high volume flow with little or no pressure differential. See US patent by Bourgeois, U.S. Pat. No. 3,191,362 as a detailed example for the technical specification of an electrostatic precipitation system. While efficiently removing agents from the air, such air purification systems do not lend themselves to collection of samples for analysis.

Filtration methods are well-known for collection of air samples for testing. Such filtration methods may also be used for capturing particles containing $(1\rightarrow3)$-$\beta$-D-glucan for assay.

Electrokinetic-based air cleaning systems have been developed and formerly commercialized by the company Sharper Image (but now discontinued) under the trade name Ionic Breeze. The original electrokinetic principle was enunciated by Brown in U.S. Pat. No. 2,949,550. This was further improved by Lee in U.S. Pat. No. 4,789,801 for improving airflow and minimizing ozone generation. Further improvements for the commercially available system are described in US patents by Taylor and Lee, U.S. Pat. No. 6,958,134; Reeves et al, U.S. Pat. No. 7,056,370; Botvinnik, U.S. Pat. No. 7,077,890; Lau et al, U.S. Pat. No. 7,097,695; Taylor et al, 7,311,762. In the foregoing descriptions of devices using electrokinetic propulsion, a common element is a high voltage electrode consisting of a wire. A very steep voltage gradient is generated orthogonally to the wire because of the very small cross-sectional area of the wire. The high voltage gradient causes the creation of a plasma consisting of charged particles, and kinetic energy is imparted to the charged particles by the high voltage gradient. The resulting net air flow is created by exchange of kinetic energy between charged and uncharged particles, and the net air flow is directed by the juxtaposition of planar electrodes which are at zero or opposite sign voltage to that of the wire electrode. Charged particles are electrostatically precipitated on to the planar electrodes, which may periodically be removed for cleaning. This body of work is directed toward air purification, not sample collection. However, as first described by Custis et al (2003), the Ionic Breeze device has been adapted for sample collection for allergen analysis by wiping down the electrodes with a paper tissue. The allergens were extracted from the tissue and subject to an immuno-assay. The Ionic Breeze was also used in the works of Peters et al (2007) and Platts-Mills et al (2005) for allergen collection for immunoassay analysis. Earlier, Parvaneh et al (2000) described an ionizer device with a "metal cup having a conductive surface as a collector plate", from which allergens are extracted for assay. It is not evident how the sample is collected on the inside of a metal cup and does not adhere to the entire surface. The device was made by Airpoint AB, Stockholm, Sweden. However, there is no public information concerning the manufacture or sale of such a product by Airpoint AB, there is insufficient information for one skilled in the art to be able to understand the details of the device, and no similar device was used by the same authors in subsequent publications on environmental allergen detection. There is no mention of focusing of the sample into a potential well created by a voltage gradient.

Yao et al (2009) and Yao and Mainelis (2006) have described methods for collection of bio-assayable agents on to an assay means or device. Yao and Manielis (2006) describe blocks of agar gel in electrical contact with planar electrodes, and Yao et al (2009) describe a microtiter plate interposed between planar electrodes. Both of these works describe a flow of air driven by a pump, and electrostatically precipitating the agents to be analyzed on to the assay means. The electrodes and the agar blocks have substantially the same area in these works.

McNerney et al (2010) describe a breathalyzer device, where the individual breathes or coughs into a breathing tube, the sample collects on the internal surface of a tube, is scraped with a plunger on to an optical biosensor, an immunological binding reaction is performed and the biosensor utilizes an evanescent wave illumination system to determine the presence or absence of *M. tuberculosis* by scattered light.

Inspirotec Inc, the Applicant herein, has commercialized an ion capture device for assay of biological materials. This and related devices are described in Inspirotec's U.S. Pat. No. 9,618,431, Electrokinetic device for capturing assayable agents in a dielectric fluid; U.S. Pat. No. 9,481,904 Electrokinetic method for capturing and bio assaying airborne assayable pathogenic agents; U.S. Pat. No. 8,038,944, Electrokinetic device for capturing assayable agents in a dielectric fluid; U.S. Pat. No. 9,360,402, Electrokinetic device for capturing assayable agents in a dielectric fluid utilizing removable electrodes; and U.S. Pat. No. 9,216,421, Integrated system for sampling and analysis). Ion capture technology may be used for capturing airborne particles containing (1→3)-β-D-glucan.

None of the prior art suggests use of the soluble fraction of (1→3)-β-D-glucan as a measure of mold exposure.

SUMMARY OF THE INVENTION (1→3)-β-d-glucan is a structural component of cell walls of molds, but can also be found in yeast, mold, pollen, bacteria. The largest fraction in the air is attributable to molds.

Assays that have been used are competitive immunoassays, sandwich immunoassays and limulus amebocyte lysate (LAL) assays. Competitive immunoassays are less sensitive, sandwich immunoassays had equivalent to LAL, and were claimed to be less sensitive and more specific. The LAL assay depends on the activation of a specific protease from horseshoe crab which creates a fluorescent signal from a synthetic substrate. The result is an extraordinarily sensitive assay. The specificity does not appear to have been an issue, and the majority of continuing work has used the commercially available LAL assay.

There have been many proposals that measurement of (1→3)-β-d-glucan is a good surrogate for total mold exposure.

A correlation was shown between levels of (1→3)-β-d-glucan in house dust and respiratory symptoms by peak expiratory flow (PEF).

In homes with active mold growth, (1→3)-β-d-glucan was found in sizes ranging from 18 to 0.18 micron. This means that a large fraction was in particles and fragments smaller than spores. The smaller range of particles are more likely to remain airborne longer and penetrate the lungs deeper, just like dust mite allergens.

As a structural cell wall component, the (1→3)-β-d-glucan is usually in an insoluble form. Therefore, all testing that has been done to date has used either an extreme heating step or an alkaline treatment to render it soluble for testing. The fact that a large fraction of the airborne form is in a range where the particles are soluble has escaped notice. We routinely remove all insoluble and particulate material from samples from our device prior to immunoassay. That fraction will contain the lower range of particulate size that will penetrate deeply into the lungs.

Alkaline extraction of this fraction has little effect on results (see examples).

Measurement of airborne soluble fraction of (1→3)-β-d-glucan is therefore both a direct measurement of a respiratory irritant whose release also parallels the release into the air of fungal allergens. None of the prior art suggests direct measurement of a free form of (1→3)-β-d-glucan in samples collected for airborne material. Measurement of the free form as a soluble fraction is the subject of this invention. This free form will represent smaller size particles which are well known to penetrate deeply into the alveoli of the lungs and thus trigger respiratory problems such as allergic reactions deep in the lungs which results in asthma. This measurement is then a parameter that parallels the behavior of allergens in general and is therefore a useful surrogate for assessing exposure to mold allergens in general.

In the preferred embodiment of the invention, the soluble fraction containing free (1→3)-β-D-glucan is collected by an electrokinetic propulsion device, for example, as commercialized by the inventors under the names Inspirotec or Exhale. However, depending on the needs, other devices well-known to those skilled in the art, such as filtration of air through filters with defined pore sizes, such as microporous membrane filters or fibrous filters, or HEPA filters or Electret filters as commercialized by the company 3M, or filters depending capture of defined size classes of particles by impaction, may be used. Examples are Anderson Impactors, and the NIOSH cyclone impactor (Lindsley et al, Journal of Environmental Monitoring, 2006, 8, 1136-42) or Spin Con wet cyclonic method or Bobcat electret-based filtration as commercialized by Alburty Labs, of Drexel, Mo.

Other objects, features, and advantages of the invention will become apparent from a review of the entire specification, including the appended claims and drawings.

BRIEF DESCRIPTION OF THE INVENTION

FIG. 1 represents a generic electrokinetic flow device.

FIGS. 2A-2D represent an assembled carrier with removable electrodes.

FIG. 3 is a graphical representation of the statistical analysis of a comparison of (1→3)-β-D-glucan compared with presence or absence of mold allergen in those same airborne samples.

FIG. 4 is a graphical representation of the statistical analysis of the comparison of (1→3)-β-D-glucan determination on a set of airborne fractions treated or not treated with NaOH.

FIG. 5 is a graphical representation of the distribution of (1->3)-β-D-glucan in 76 homes throughout the United States.

DETAILED DESCRIPTION OF THE INVENTION

Air is sampled by a sampling device which maybe as described in detail in prior patents issued to the Applicant, namely U.S. Pat. Nos. 8,038,944, 9,216,421, 9,360,402, 9,481,904 and 9,618,431. The specification of each of these patents is incorporated by reference herein. Particular attention is drawn to U.S. Pat. No. 9,360,402 for the analysis of bio-specific material using a cartridge with removeable electrodes. This device provides the convenience of extraction of the bio-specific agents by immersing the detached electrodes directly in buffer extraction medium and shaking in a centrifuge tube with a vortex mixer, as is described in detail below.

Example 1

FIG. 1 represents a basic ion propulsion device with a housing, 1, with high voltage wire seen in cross-section, 2, and symbolic representation of voltage contours, grounded plate electrodes 3. Resulting ion flow is represented by arrow 4. Resulting net air in-flow is represented by arrow 5 and outflow by arrows 6. Advantageously, the electrodes 3 are removable and may be mounted to a carrier, which is removable from the housing 1, as shown in U.S. Pat. No. 9,360,402.

Example 2

FIGS. 2A and 2B illustrates a removable carrier assembly 21 that could be used with the housing of FIG. 1 as an alternative to fixed electrodes. The carrier assembly 21 is described in detail in U.S. Pat. No. 9,360,402. The carrier assembly 21 includes a one-piece plastic carrier 23, a latch 25 and capture electrodes 27. The carrier 23 is removeable from the housing 1. Moreover, the capture electrodes 27 are removably secured to the carrier 23. The latch 25 supports the electrodes 27, see FIGS. 2C and 2D. The latch 25 is adapted to secure the capture electrodes 27 to the carrier 23. For testing, the carrier 23 can be removed from the housing 1. The latch 25 and electrodes 27 can then be removed from the carrier 23 to facilitate testing.

Example 3

Samples were run in a variety of mold positive and mold negative home environments. The presence of airborne mold allergens were determined by multiplex immunoassays using MARIA kits from Indoor Biotechnologies and the MagPix instrument supplied by BioRad Inc. Samplers were routinely run for 5 days and the allergens and (1→3)-β-D-glucan containing material extracted from the detached electrodes as described in detail in Example 4, and the supernatants tested by MARIA and by Glucatell assay kit (Associates of Cape Cod Inc., East Falmouth, Mass.) following manufacturers protocol for kinetic rate assay.

Figure 3:
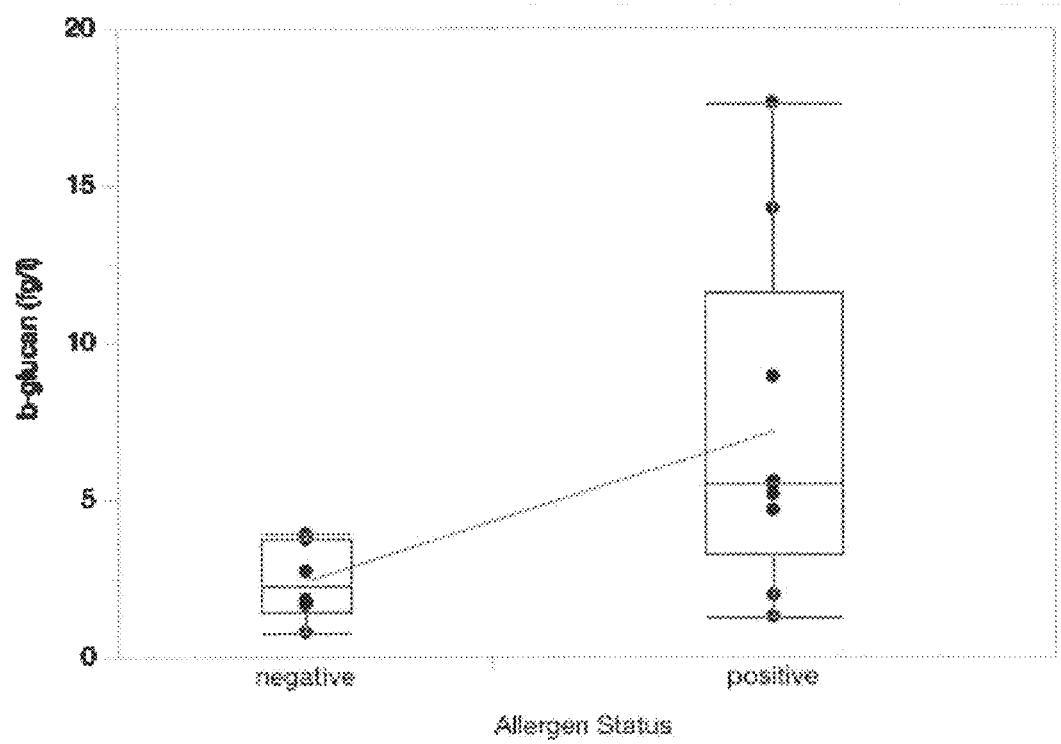

FIG. 3 shows a statistical analysis of comparison of presence of mold allergens determined by the MARIA™ multiplex immunoassay method for the mold allergens Alt a 1 and Asp f 1) and (1→3)-β-D-glucan. The box plots show the 90 percentile ranges and the full range of values. The results summarized in FIG. 3 show a significant relationship between the absence of mold allergen and the absence of (1→3)-β-D-glucan in the airborne samples. A higher mean is also observed in the mold allergen positive group (7.19) compared to the negative group (2.42). Data from FIG. 3 shows a possible significant relationship between airborne mold allergen and the presence of (1→3)-β-D-glucan.

Example 4

Effect of NaOH extraction on measured (1→3)-β-D-glucan.

TABLE 1

| Sample | NaOH Treated (fg/L) | NaOH Untreated (fg/L) |
|---|---|---|
| 1 | 9.49 | 5.86 |
| 2 | 21.60 | 15.28 |
| 3 | 4.75 | 7.02 |
| 4 | 3.36 | 3.96 |
| 5 | 4.27 | 2.05 |
| 6 | 3.83 | 4.10 |

The Inspirotec air sampling device, described above, was run for 5 consecutive days in each test environment. Following testing, stainless steel electrode strips were removed from cartridges, located in the device, and transferred to 15 ml centrifuge tubes. One ml of PBS with 0.02% TWEEN® 20 was added to the tubes and vortexed intermittently over 10 minutes. Samples were removed from the centrifuge tubes and transferred to 2 mL screw-cap tubes, then centrifuged at 15,000 g for 30 minutes. The supernatants were removed and placed in new 2 ml screw-cap tubes. In another 2 mL screw-cap tube, 80 µl of these samples were brought to 0.05N NaOH by addition of 20 uL of 2.5N NaOH. Samples were shaken for 2.5 hrs at room temperature o an orbital shaker, neutralized by addition of 100 µL of 2M Tris-HCL (1M Tris-HCL final). (1→3)-β-D-glucan levels were determined using the Glucatell assay kit (Associates of Cape Cod Inc., East Falmouth, Mass.) following manufacturer's standard protocol for kinetic rate assay.

The results are also shown graphically in FIG. 3 as analyzed statistically with the JMP package, JMP® Pro 13.0.0 (SAS Institute Inc. Cary, N.C.).

The slope of the best fit straight line is 1.41. This shows that when samples are collected and analyzed in this manner, 41% of the (1→3)-β-D-glucan is in an insoluble fraction. The current invention focuses attention on the soluble fraction, as determined by the supernatant from centrifugation and no extraction.

Example 5

Distribution of (1→3)-β-D-glucan levels in homes throughout the U.S.

Air samples were collected from 76 homes across the United States, using the Inspirotec device. In each home, the device was run for a period of 1 to 5 days. After completion of running period, stainless steel electrode strips were removed from cartridges, located in the device, and transferred to 15 mL centrifuge tubes. One mL of 1×PBS with 0.02% Tween® 20 was added to the tubes and vortexed intermittently over a period of 10 minutes. Samples were removed from 15 mL centrifuge tubes and transferred to 2 mL screw-cap tubes. They were then centrifuged at 15,000 g for 30 minutes. The supernatants were removed and placed in new 2 mL screw-cap tubes. (1→3)-β-D-Glucan concentration was measured using the Glucatell assay kit (Associates of Cape Cod Inc., East Falmouth, Mass.) following manufacturers protocol for kinetic rate assay.

Figure 4:
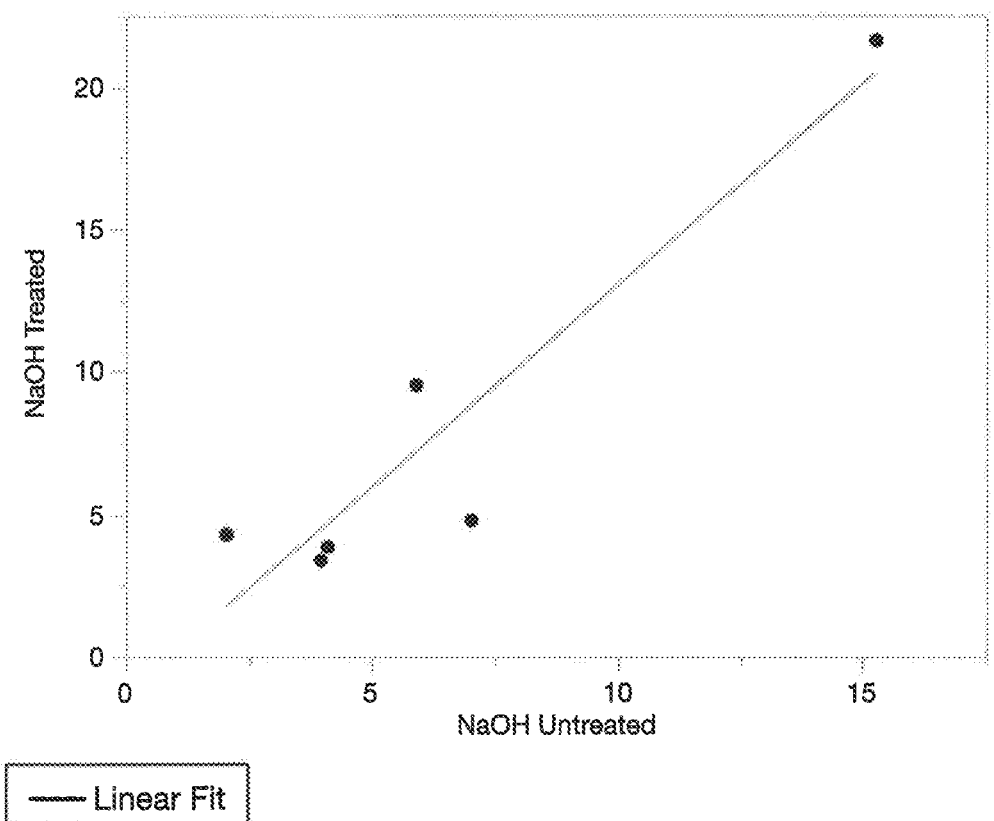
Figure 5:
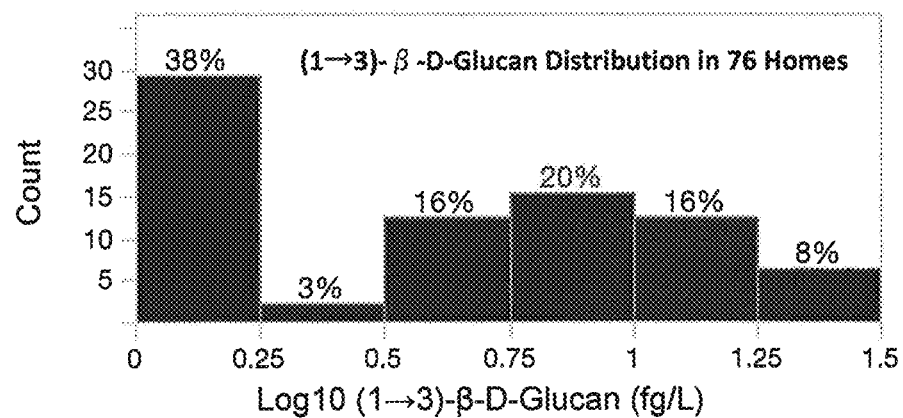

The Results are shown graphically in FIG. 4 as analyzed statistically with the JMP package, JMP® Pro 13.0.0 (SAS Institute Inc. Cary, N.C.). Values below the mean values of zero time field controls for the assay were assigned a value of field control/2 and number of occurrences of $\log_{10}$ of the values were plotted in bins as shown on the x-axis.

(1→3)-β-D-Glucan was detected in 62% of homes.

It is apparent from the foregoing that measurement of (1→3)-β-D-Glucan in the soluble fraction of samples collected from airborne material is a representation of the fraction of free (1→3)-β-D-Glucan in the air that is material released from actively growing molds and will penetrate most deeply into the respiratory system with impact on respiratory health. This fraction may also parallel the release of allergens from molds so that it is also be a surrogate assay for airborne allergen exposure. Previous art ignored the soluble fraction and focused on material extractable from larger complexes. It will be obvious to those skilled in the art that the soluble fraction may be prepared by the preferred method of centrifugation as described here, or by other well known methods such as filtration or settling.

Thus, there is described herein a method for analyzing aerosol particles, wherein said aerosol particles are captured by an air sampling device, extracted from the sampling medium and soluble fraction analyzed for (1→3)-β-D-glucan. The air sampling device may be based on electrokinetic propulsion or on electrostatic precipitation. (1→3)-β-D-glucan may be determined by a limulus-amebocyte based assay or by an immunoassay. The sampling device may be based on filtration, on impingement, or on an impactor.

There is also described a method for analyzing aerosol particles, wherein said aerosol particles are deposited on an electrode of an electrokinetic propulsion device from a volume of air propelled electrokinetically through said device, said electrode being removably attached to a carrier mounting; said electrode is removed from said carrier mounting and placed in an extraction vessel; a predetermined volume of extraction fluid is added to said extraction vessel; said electrode is agitated in said extraction fluid for a predetermined time; and all or part of said extraction fluid is added to a reaction mixture for analysis of said aerosol particles for (1→3)-β-D-glucan.

What we claim is:

1. A method for analyzing aerosol particles, comprising capturing aerosol particles using an air sampling device, suspending said captured aerosol particles from the air sampling device in a extraction fluid, performing centrifugation of said suspension, directly adding with no other processing all or part of supernatant from said centrifugation to a reaction mixture for analysis of said supernatant for (1→3)-β-D-glucan.

2. A method according to claim 1 wherein the air sampling device is based on electrokinetic propulsion.

3. A method according to claim 1 where the sampling device is based on electrostatic precipitation.

4. A method according to claim 1 comprising determining (1→3)-β-D-glucan level by a limulus-amebocyte based assay.

5. A method according to claim 1 comprising determining (1→3)-β-D-glucan level by an immunoassay.

6. A method according claim 1 wherein the sampling device is based on filtration.

7. A method according claim 1 wherein the sampling device is based on impingement.

8. A method according claim 1 wherein the sampling device is based on an impactor.

9. A method for analyzing aerosol particles, comprising: capturing aerosol particles on an electrode of an electrokinetic propulsion device from a volume of air propelled electrokinetically through said device, said electrode being removably attached to a carrier mounting; removing said electrode from said carrier mounting and placing said electrode in an extraction vessel; adding a predetermined volume of extraction fluid to said extraction vessel; agitating said electrode in said neutral extraction fluid for a predetermined time; and directly adding with no other processing all or part of said neutral extraction fluid to a reaction mixture for analysis of said aerosol particles for (1→3)-β-D-glucan.

10. A method according to claim 9 comprising determining (1→3)-β-D-glucan level by a limulus-amebocyte based assay.

11. A method according to claim 9 comprising determining (1→3)-β-D-glucan level by an immunoassay.

* * * * *